United States Patent [19]

Ticknor

[11] Patent Number: 4,465,462
[45] Date of Patent: Aug. 14, 1984

[54] GINGIVAL RETRACTION CORD

[76] Inventor: Verne E. Ticknor, 333 N. Shore Dr., South Haven, Mich. 49090

[21] Appl. No.: 489,190

[22] Filed: Apr. 27, 1983

[51] Int. Cl.³ .............................................. A61C 5/14
[52] U.S. Cl. ..................... 433/136; 433/215; 132/93; 604/1
[58] Field of Search ............. 433/136, 215, 40; 132/89, 93; 128/20, 759; 604/1; 428/373, 398

[56] References Cited

U.S. PATENT DOCUMENTS

| 2,846,927 | 8/1958 | Masci et al. | 433/136 |
| 3,151,393 | 10/1964 | Holmes | 433/40 |
| 3,238,620 | 3/1966 | Robertson | 433/40 |
| 3,390,458 | 7/1968 | Lytton | 433/40 |
| 3,541,689 | 11/1970 | Snead | 433/40 |
| 4,198,977 | 4/1980 | Aoki | 433/136 |
| 4,321,038 | 3/1982 | Porteous | 433/136 |

FOREIGN PATENT DOCUMENTS 1184245 7/1959 France ................... 433/136

Primary Examiner—John J. Wilson
Attorney, Agent, or Firm—Price, Heneveld, Huizenga & Cooper

[57] ABSTRACT

The specification discloses a gingival retraction cord having a tapered diameter throughout its length and having a length sufficient to enable the cord to be wrapped several times about a tooth. In use, the cord, starting with its smaller end, is spirally wrapped and packed about a tooth between the tooth and surrounding gingival tissue to form a flared gingival crevice.

11 Claims, 7 Drawing Figures

GINGIVAL RETRACTION CORD

BACKGROUND OF THE INVENTION

The present invention relates to dental devices, and more particularly to gingival retraction cords.

In dental treatment, it is often necessary to retract gingival tissue from a tooth in order to prepare the patient for taking impressions, setting crowns, or effecting restorations. Typically, the retractions are made using gingival retraction cords fabricated of cotton and impregnated with a therapeutic preparation.

One known method of effecting a gingival retraction is illustrated in FIG. 1 of the drawings, wherein tooth 110 is shown prepared for the installation of a crown and includes roots 112 and 114 extending into gingival tissue 116. Gingival crevice 118 is located between tooth 110 and gingival tissue 116 and is retracted from tooth 110 by packing cords 120 into crevice 118. Suitable cords include those manufactured by Pascal Company, Incorporated of Bellevue, Wash., under the trademark PASCORD, SUPER PAK, RACORD, and HEMAL-PAK. Generally, retraction cord is sold in bulk in three standard sizes or diameters, specifically No. 8, No. 9, and No. 10. In retracting gingival tissue 116, gingival crevice 118 preferably flares outwardly from bottom 118a to top to facilitate the taking of impressions and moldings thereabout. Therefore, a first length of No. 8 small diameter retraction cord 122 is unspooled from a bulk container, cut to the appropriate length, and packed about tooth 110 in gingival crevice 118. Second, a length of No. 9 or medium diameter cord 124 is unspooled from the bulk container, cut to a predetermined length, and packed in gingival crevice 118 on top of small diameter cord 122. Finally, a length of No. 10 large diameter cord 126 is unspooled and cut from a third bulk container, and packed in gingival crevice 118 on top of medium diameter cord 124. After a period of time, approximately five minutes, the cords are removed and the impression material is injected around the tooth 110, and particularly into gingival crevice 118, to complete the molding operation. Known flexible retraction apparatuses used are illustrated in U.S. Pat. No. 4,321,038, entitled BRAIDED GINGIVAL RETRACTION CORD and issued Mar. 23, 1982, to Porteous (braided cotton cord); and U.S. Pat. No. 3,238,620, entitled METHOD OF PREPARING AN IMPRESSION OF A TOOTH and issued Mar. 8, 1966, to Robertson (leather ring).

However, known gingival retraction materials and methods are not without their drawbacks. First, known cords are typically sold in bulk, spooled within a dispensing container. Consequently, removing the cord from the containers and judging and cutting appropriate lengths are time-consuming and laborious. The cord often becomes entangled with itself within the container making removal difficult or even impossible. Second, two or three separate cords are often required to effect the tissue retraction, further creating inconvenience and delays.

SUMMARY OF THE INVENTION

The aforementioned problems are solved by the present invention comprising a single gingival retraction cord enabling a flared gingival crevice to be formed during tissue retraction. More particularly, the cord is of sufficient length to be wrapped about a tooth several times and includes a starter end having a first size cross section and an opposite end having a second and larger size cross section. The cross section of the cord increases throughout its length from the starter end to the opposite end. The cord is used to effect tissue retraction by first packing the starter end between a tooth and the gingival tissue to be retracted, and then wrapping and packing the cord about the tooth in spiral fashion. Because the cord increases in cross-sectional size from the starter end to the opposite end, the gingival crevice is formed as a V-shape as the cord is wrapped and packed spirally about the tooth.

The cord of the present invention eliminates the need to unspool, untangle, cut, and form bulk retraction cord into separate rings for packing about the tooth. Second, the cord enables the formation of a V-shaped or flared gingival crevice in gingival tissue retraction using a single cord.

In a preferred embodiment of the invention, an enlarged starter ball is included at the starter end to facilitate securement of the starter end in the gingival crevice. More specifically, the starter ball has a cross section larger than that of the starter end, such that the starter ball serves as an anchor to reduce the possibility of accidentally pulling the starter end out of the crevice during packing of the cord. In this more restrictive embodiment, the frustrations of the packed cord pulling out of the gingival crevice are greatly reduced.

These and other objects, advantages, and features of the invention will be more readily understood and appreciated by reference to the specification and drawings.

DETAILED DESCRIPTION OF THE PREFERRED EMBODIMENT

Figure 1:
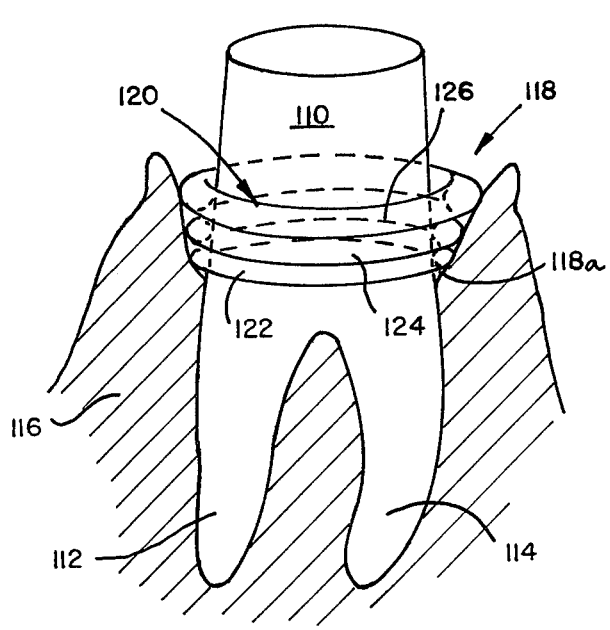
FIG. 1 is a fragmentary, partially sectional view of a gingival retraction prepared using known retraction cords.

A gingival retraction cord constructed in accordance with a preferred embodiment of the invention is illustrated in FIGS. 2–5 and generally designated 10. The cord includes relatively small diameter starter end 12 and a relatively large diameter opposite end 14. As can be seen in FIG. 3C, small end 12 is generally circular in cross section having a diameter approximating the diameter of a standard No. 8 retraction cord (i.e., 0.8 mm). As seen in FIG. 3A, opposite end 14 is also generally circular in cross section and has a second diameter larger than the diameter of starter end 12 and approximating the diameter of a No. 10 retraction cord (i.e., 1.3 mm). The cross-sectional size of starter end 12 is therefore smaller than the cross-sectional size of opposite end 14.

Retraction cord 10 increases in cross-sectional size or diameter from starter end 12 to opposite free end 14. In the preferred embodiment, the diameter increases generally uniformly from the starter end to the opposite end such that the diameter of cord 10 at midpoint 16 (see also FIG. 3B) is approximately midway between the diameters of the starter end (i.e., approximately 1.0 mm) and the opposite end. Although the preferred construction calls for a generally uniformly increasing cross section, the diameter may increase nonuniformly, for example, in steps.

The material of which cord 10 is fabricated can vary widely. In the preferred embodiment, cord 10 is fabricated of a braided absorbent material, such as cotton, similar to the Pascal Company, Incorporated cords noted in the Background of the Invention. Absorbent cords may optionally be impregnated with medication, such as epinephrine. In another embodiment, the cord is fabricated of silk; however, this material has relatively little absorbency. In yet another embodiment, the cord is fabricated of a monofilament line, somewhat similar to monofilament tapered lines commonly used in fly fishing. The preferred cross-sectional shape of cord 10 is circular, which is believed to be the easiest and most inexpensively manufactured shape, and which also facilitates packing the cord about a tooth.

The length of cord 10 varies with the size tooth involved in the retraction and preferably is sufficient to wrap around the tooth several times, and more preferably at least three times. Cords suitable for use on an average adult molar would be approximately three inches or 75 mm in length, while cords suitable for use on adult bicupspids would be approximately two inches or 50 mm length. As noted above, the diameter of starter end 12 of each cord 10 approximates the diameter of a No. 8 retraction cord, while the diameter of opposite end 14 approximates the diameter of a No. 10 retraction cord.

Starter ball 18 is a generally spherical mass secured to starter end 12 and has a cross-sectional size or diameter larger than that of the starter end. When cord 10 is fabricated of a monofilament material as illustrated, starter ball 18 may be formed integrally with starter end 12. When cord 10 is fabricated of an absorbent material, ball 18 can be formed by tying a knot in starter end 12. Starter ball 18 may also comprise a separate element secured to starter end 12 in virtually any fashion. Starter ball 18 may be optionally omitted from cord 10.

METHOD OF USE

Figure 4:
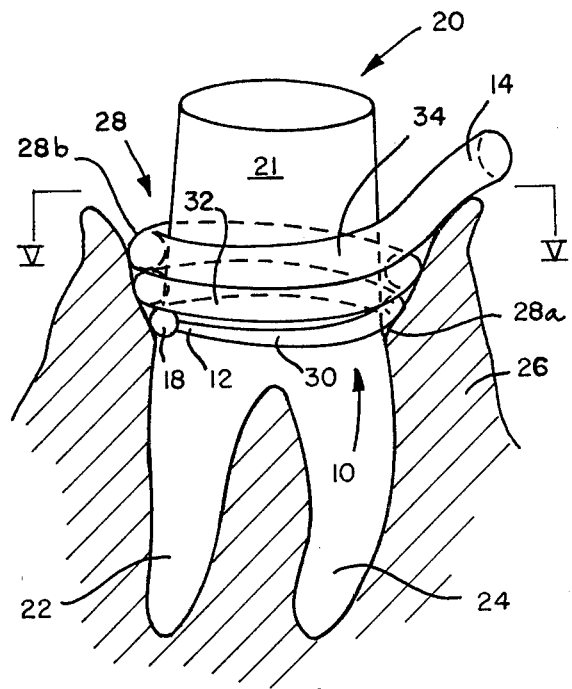
FIG. 4 is a fragmentary, partially sectional view of a gingival retraction prepared using the gingival retraction cord of the present invention.
Figure 2:
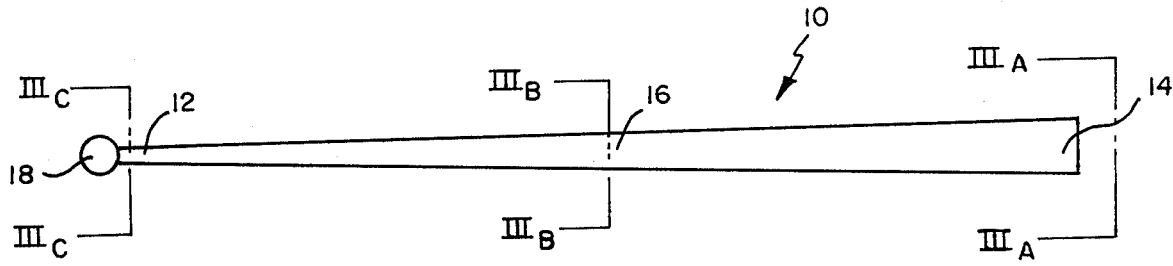
FIG. 2 is a plan view of the gingival retraction cord of the present invention.
Figure 3A:
FIG. 3A is an end view of the cord taken along plane IIIA—IIIA in FIG. 2.
Figure 3B:
FIG. 3B is a sectional view of the cord taken along plane IIIB—IIIB in FIG. 2.
Figure 3C:
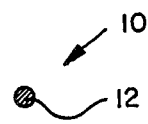
FIG. 3C is a sectional view of the cord taken along plane IIIC—IIIC in FIG. 2.
Figure 5:
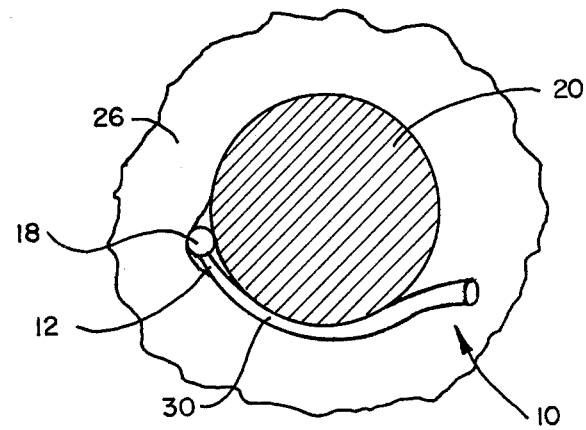
FIG. 5 is a sectional view taken along plane V—V in FIG. 4 showing the gingival retraction cord initially inserted into the gingival crevice.

Use of the present gingival retraction cord 10 is illustrated in FIGS. 4 and 5. Tooth 20 includes crown 21 prepared for the taking of an impression, and roots 22 and 24 extend into gingival tissue 26. Gingival crevice 28 is located between tissue 26 and tooth 20.

After crown 21 of tooth 20 has been prepared as illustrated in FIG. 4 for an impression, cord 10 of the present invention is packed about the tooth in spiral fashion. First, anchor ball 18 is forced between tooth 20 and tissue 26 (FIGS. 4 and 5) to anchor starter end 12 of cord 10 in position. Cord 10 is then wrapped and packed spirally upon itself several times. As illustrated in FIG. 4, cord 10 is shown wrapped two and one-half times about tooth 20. Packing is completely by completing the third wrap 34. Because the diameter of cord 10 is tapered, gingival crevice 28 has a V or flared shape comprising a relatively narrow end 28a and a relatively wide upper end 28b. More particularly, each revolution of cord 10 increases sequentially in diameter such that first revolution 30 is similar in size to a No. 8 cord, second revolution 32 is similar in size to a No. 9 cord, and revolution 34 is similar in diameter to a No. 10 cord. After retracted tissue 26 has been allowed to set, cord 10 is removed from the tooth and an impression is made utilizing procedures well known to those having ordinary skill in the art.

The above description is that of preferred embodiments of the invention. Various changes and alterations can be made without departing from the spirit and broader aspects of the invention as set forth in the claims, which are to be interpreted in accordance with the principles of patent law, including the doctrine of equivalents.

The embodiments of the invention in which an exclusive property or privilege is claimed are defined as follows:

1. A flexible, nondisintegrating gingival retraction cord generally circular in cross section and including a starter end and a remote opposite end, the length of said cord being at least approximately 50 mm so that said cord can be wrapped about a tooth two or more times, said starter end having a first diameter of approximately 0.8 mm, said opposite end having a second diameter of approximately 1.3 mm, and said cord increasing generally uniformly in diameter from said starter end to said opposite end, whereby, as said cord is spirally packed about a tooth beginning with said starter end, said cord creates a V-shaped gingival retraction crevice between the tooth and surrounding gum.

2. A gingival retraction cord as defined in claim 1 further comprising an anchor secured to said starter end and having a cross section larger than that of said starter end, said anchor facilitating securement of said starter end between the tooth and the gingival tissue.

3. A gingival retraction cord as defined in claim 1 wherein said length of said cord is at least approximately 75 mm so that said cord can be wrapped about a tooth three or more times.

4. A gingival retraction cord as defined in claim 1 wherein said cord is fabricated of a braided absorbent material.

5. A gingival retraction cord as defined in claim 1 wherein said cord is fabricated of silk.

6. A gingival retraction cord as defined in claim 1 wherein said cord is fabricated of monofilament line.

7. A method of retracting gingival tissue about a tooth comprising:
providing a cord including a starter end having a first cross-sectional size and an opposite free end having a second larger cross-sectional size, said cord increasing in cross-sectional size from said starter end to said opposite free end;
packing said starter end between the tooth and the surrounding gingival tissue; and
packing said cord in spiral fashion about the tooth, whereby the gingival tissue is retracted by said cord to form a flared gingival crevice.

8. A method of retracting gingival tissue as defined in claim 7 further comprising including a starter ball at said starter end of said cord, said starter ball being larger in cross-section than said starter end; and wherein said first packing step comprises packing said starter ball between the tooth and gingival tissue.

9. A method of retracting gingival tissue as defined in claim 7 wherein said cord providing step comprises providing a cord having a generally uniformly increasing cross-sectional size between said starter and opposite ends.

10. A method of retracting gingival tissue as defined in claim 9 wherein said cord providing step further comprises providing a cord having a generally circular cross section throughout its length.

11. A method of retracting gingival tissue as defined in claim 7 wherein said cord providing step further comprises providing a cord having a generally circular cross section throughout its length.

* * * * *

UNITED STATES PATENT AND TRADEMARK OFFICE
CERTIFICATE OF CORRECTION

PATENT NO. : 4,465,462

DATED : August 14, 1984

INVENTOR(S) : Verne E. Ticknor

It is certified that error appears in the above-identified patent and that said Letters Patent is hereby corrected as shown below:

Column 1, lines 21-22:
"trademark" should be --trademarks--;

Column 3, lines 9-10:
"the diameters of the starter end (i.e., approximately 1.0 mm) and the opposite end. Although the preferred con-" should be --the diameters of the starter end and the opposite end (i.e., approximately 1.0 mm). Although the preferred con---; and Column 3, line 66:
"completely" should be --completed--.

Signed and Sealed this

Twenty-sixth Day of February 1985

[SEAL]

Attest:

DONALD J. QUIGG

Attesting Officer     Acting Commissioner of Patents and Trademarks